United States Patent [19]
Rill et al.

[11] Patent Number: 5,811,307
[45] Date of Patent: Sep. 22, 1998

[54] DICATIONIC PERYLENE DYE FOR PRECIPITATION AND QUANTITATION OF DNA

[75] Inventors: Randolph L. Rill; Zhi-Ren Liu, both of Tallahassee, Fla.

[73] Assignee: Florida State University, Tallahassee, Fla.

[21] Appl. No.: 873,222

[22] Filed: Jun. 11, 1997

Related U.S. Application Data

[62] Division of Ser. No. 584,928, Jan. 11, 1996, abandoned.

[51] Int. Cl.[6] ......................... G01N 33/48; G01N 33/487
[52] U.S. Cl. .............................. 436/94; 436/86; 436/175; 436/63
[58] Field of Search ................ 436/86–93, 175, 436/63, 71, 94

[56] References Cited

U.S. PATENT DOCUMENTS

| | | | |
|---|---|---|---|
| 3,661,912 | 5/1972 | Kalz et al. | 260/281 |
| 3,871,882 | 3/1975 | Wiedemann | 96/1.5 |
| 4,262,851 | 4/1981 | Graser et al. | 241/16 |
| 4,667,036 | 5/1987 | Iden et al. | 546/37 |
| 4,709,029 | 11/1987 | Spietschka et al. | 544/125 |
| 4,746,741 | 5/1988 | Staudenmayer | 546/37 |
| 4,762,569 | 8/1988 | Miki et al. | 106/476 |
| 4,801,550 | 1/1989 | Kapuscinski et al. | 436/94 |
| 4,831,140 | 5/1989 | Spietschka et al. | 546/37 |
| 4,906,749 | 3/1990 | Theodoropulos | 544/69 |
| 4,975,365 | 12/1990 | Grossman et al. | 436/63 |
| 4,978,625 | 12/1990 | Wagner et al. | 436/518 |
| 4,978,755 | 12/1990 | Bäbler | 546/37 |
| 5,010,183 | 4/1991 | Macfarlane | 536/27 |
| 5,013,627 | 5/1991 | Harnisch et al. | 430/110 |
| 5,026,840 | 6/1991 | Dattagupta et al. | 536/27 |
| 5,104,918 | 4/1992 | Bäbler | 524/90 |
| 5,106,966 | 4/1992 | Thomas et al. | 536/27 |
| 5,110,931 | 5/1992 | Dietz et al. | 546/37 |
| 5,123,966 | 6/1992 | Dietz et al. | 106/498 |
| 5,132,432 | 7/1992 | Haugland et al. | 548/518 |
| 5,247,088 | 9/1993 | Flatt | 546/37 |
| 5,248,774 | 9/1993 | Dietz et al. | 544/125 |
| 5,264,034 | 11/1993 | Dietz et al. | 106/493 |
| 5,292,638 | 3/1994 | Benz et al. | 436/63 |
| 5,319,083 | 6/1994 | Tröster | 546/37 |
| 5,321,130 | 6/1994 | Yue et al. | 536/23.1 |
| 5,332,666 | 7/1994 | Prober et al. | 435/91.5 |
| 5,359,092 | 10/1994 | Hay et al. | 546/99 |
| 5,366,860 | 11/1994 | Bergot et al. | 435/6 |
| 5,405,951 | 4/1995 | Woodard | 536/25 |

OTHER PUBLICATIONS

Zhi–Ren Liu and R.L. Rill, Chemical Abstracts, vol. 124 No. 19, issued May 6, 1996, p. 662, [Bis 3, 4, 9, 10 Perylene-tetracarboxylic Dimide], a dicationic perylene dye for rapid precipitation and quantitation of trade amounts of DNA Anal. Biochem. vol. 236, No. 1 pp. 139–145. (Eng.).

*Primary Examiner*—Lyle A. Alexander
*Attorney, Agent, or Firm*—Senniger, Powers, Leavitt & Roedel

[57] ABSTRACT

The novel dicationic dye N,N'-bis[3,3'-(dimethylamino) propylamine]-3,4,9,10-perylenetetracarboxylic diimide (DAPER) is prepared by reacting 3,4,9,10-perylenetetracarboxylic dianhydride with N,N-dimethylaminopropylamine. The dye DAPER is particularly useful in a rapid, sensitive method for the precipitation, recovery and quantitation of DNA from solutions containing DNA, which method involves the steps of (a) adding the dye DAPER to a solution containing DNA and allowing the resulting mixture to equilibrate; (b) collecting the resulting precipitate; (c) removing weakly bound DAPER from the precipitate; (d) extracting DAPER therefrom by the addition of a solvent therefor; and (e) determining the amount of DNA precipitated by measuring either the absorbance or fluorescence of DAPER in the solvent extract from step (d).

3 Claims, 7 Drawing Sheets

DICATIONIC PERYLENE DYE FOR PRECIPITATION AND QUANTITATION OF DNA

This is a division of application Ser. No. 08/584,928, filed Jan. 11, 1996 now abandoned.

BACKGROUND OF THE INVENTION

This invention relates a dye for the recovery and quantitation of DNA and, more particularly, to a novel dicationic dye with a polycyclic aromatic perylene core and flexible cationic side chains which is useful for the rapid precipitation, recovery and quantitation of trace amounts of DNA.

The isolation and analysis of trace amounts of DNA are essential in many biological, recombinant DNA, and biotechnology experiments. Conventional precipitation methods employing ethanol or isopropanol are not optimal for experiments requiring sub-microgram scale DNA isolation; often being incomplete, time consuming and requiring high salt concentrations necessitating desalting prior to further use. Although improvements have been described (Shapiro, D. J., 1981, Anal. Biochem. 110, 229), a high salt concentration and high speed ultracentrifuge are still needed. Cationic detergents such as cetyl-trimethylammonium bromide (Cetavlon) have been recommended as DNA and RNA isolation reagents (Guerritore, D. and Bellelli, L., 1959, Nature 184, 1636–1638), but potential drawbacks are the sensitivity to salt concentrations in excess of 0.3M, in which the DNA-detergent complex becomes partially soluble (Osika, V. D. et al., 1975, Doklady Akademii Nauk SSSR 224, 707–709), and the lack of methods for monitoring residual detergent. Additional methods have also been reported (Ross, J. A. et al., 1991, Nucleic Acids Res. 19, 6053–6055), but none can be used to simultaneously isolate and quantitate sub-microgram amounts of DNA.

There are sensitive methods to analyze DNA by using one of several fluorescent dyes. For example, Hoechst 33258 is a commonly used DNA groove binding dye available in a DNA analysis kit (Hoefer Scientific Instruments). This method is dependent on the DNA type, however, because the dye binds sequence-selectively and the fluorescence enhancement is largely dependent on the A-T content (Stokke, T. and Steen, H. B., 1985, J. Histochem. Cytochem. 33, 333–338). All such methods render the DNA used for analyses essentially unavailable, which can be a major limitation when working with trace amounts.

Perylenetetracarboxylic acid diimides, analogs thereof and perylene analogs are disclosed in U.S. Pat. Nos. 5,248,774, 3,871,882, 4,667,036, 4,262,851, 5,264,034, 4,831,140, 4,978,755, 5,104,918 and 5,132,432.

There is a continuing need for improved dyes useful for rapid and simultaneous recovery and quantitation of DNA and which permit the quantitation to be done by either fluorescence or absorbance depending on the amount of DNA precipitated.

SUMMARY OF THE INVENTION

Among the several objects of the invention may be noted the provision of a novel dicationic dye which is useful to precipitate extremely low concentrations of DNA rapidly, efficiently and with a stoichiometry of one tightly bound dye per DNA base pair, corresponding to an uncharged complex; the provision of such a novel dye which provides the basis for a very sensitive, rapid and versatile method for simultaneous precipitation and quantitation of microgram and sub-microgram amounts of DNA; the provision of a process for preparing such a novel dye; and the provision of processes for the precipitation, recovery and quantitation of DNA utilizing said novel dye. Other objects and features will be in part apparent and in part pointed out hereinafter.

Briefly, the present invention is directed to the novel dicationic dye N,N'-bis[3,3'(dimethylamino) propylamine]-3,4,9,10-perylenetetracarboxylic diimide (DAPER). The invention is also directed to a process for preparing this novel dicationic dye by reacting 3,4,9,10-perylenetetracarboxylic dianhydride with N,N-dimethylamino-propylamine. Further, the invention is directed to a process for the precipitation, recovery and quantitation of DNA from solutions containing DNA which comprises the steps of (a) adding the dye DAPER to a solution containing DNA and allowing the resulting mixture to equilibrate; (b) collecting the resulting precipitate; (c) removing weakly bound DAPER from the precipitate; (d) extracting DAPER therefrom by the addition of a solvent therefor; and (e) determining the amount of DNA precipitated by measuring either the absorbance or fluorescence of DAPER in the solvent extract from step (d).

Description of the Preferred Embodiments

In accordance with the present invention, it has been found that the novel dicationic dye N,N'-bis[3,3'-(dimethylamino)propylamine]-3,4,9,10-perylenetetracarboxylic diimide having the following structure:

exhibits unique association and spectroscopic properties rendering it particularly useful in a rapid, sensitive method for DNA precipitation, recovery and quantitation. The compound DAPER, a perylene diimide, has a hemi-aromatic core of seven, six-membered fused rings which provide a unique amphiphilic agent when combined with cationic side chains. A total of 28π electrons are distributed on the fused ring systems, but molecular orbital calculations indicate that perylene and its derivatives are not fully aromatic. Full aromaticity can be achieved by gain or loss of an electron from the perylene ring, which promote charge transfer interactions in molecular stacks with appropriate donors or acceptors. On the other hand, the +2 charge on protonated DAPER confers high water solubility. This juxtaposition of flexible polar arms and extended aromatic ring systems is believed to promote ring stacking in water in a manner reminiscent of base stacking in polynucleotides.

The novel DAPER compound of the invention may be conveniently prepared by reacting 3,4,9,10-perylene-tetracarboxylic dianhydride with N,N-dimethyl-aminopropylamine. More specifically, a reaction mixture of 3,4,9,10-perylentetracarboxylic dianhydride and N,N-dimethylaminopropylamine is mildly refluxed in the presence of a solvent for the mixture, then distilled under reduced pressure to remove the solvent. The resulting residue is dissolved in water and insoluble compounds are removed by filtration. The pH of the resulting solution is adjusted to about 3 and precipitated byproducts are removed by filtration. The pH of the resulting solution is adjusted to about 10 and the precipitated DAPER product is recovered by filtration, washed with water and vacuum dried.

In accordance with the invention, it has been found that the unique properties of the novel compound DAPER provide the basis for a sensitive, rapid and versatile method for the simultaneous precipitation, recovery and quantitation of DNA in microgram and sub-microgram amounts. Thus, DAPER completely precipitates DNA from solutions with concentrations≧100 ng/ml at salt concentrations≦0.5SM with a defined DNA base: DAPER stoichiometry, i.e. precipitation is first noted at a DNA: DAPER ratio of 3:1 (moles DNA base per mole dye) and is complete at a ratio of 2:3. DNA fragments as small as 68 bp may be recovered quantitatively through the practice of the present invention, and recovered DNA may be readily digested by restriction endonucleaseas and end-labeled with AMV reverse transcriptase. Advantageously, ultra-high speed centrifugation, high salt concentration and prolonged storage of solutions at low temperature are not required. Since the DAPER dye can be back-extracted into a standard phenol:chloroform:isoamyl alcohol mixture, the amount of DNA precipitated is readily quantitated by examination of the extracts, while the DNA is recovered in aqueous solution. The process of the invention also permits quantitation to be performed by visible absorbance measurements on a microgram scale, and by fluorescence measurements on a nanogram scale.

In carrying out the practice of the invention, a stock solution of DAPER is added to a DNA solution and the resulting mixture is allowed to equilibrate. The resulting precipitate is collected as by centrifugation and the weakly bound excess DAPER dye is removed by washing the precipitate with water. The washed precipitate is then resuspended and the DAPER dye is extracted therefrom by the addition of a solvent for DAPER. Various solvents for DAPER such as chloroform, phenol:chloroform and dimethylformamide may be used, it being understood that other solvents for DAPER may also be employed in extracting DAPER from the DNA-containing precipitate. A phenol:chloroform mixture is more efficient than either phenol or chloroform alone. After extraction of DAPER, the aqueous phase containing DNA is removed and may be further extracted with ethyl ether, for example, to remove phenol if the recovered DNA is to be used for enzyme reactions. Samples of the aqueous phase containing DNA may be applied directly to gels for electrophoresis.

Figure 1:
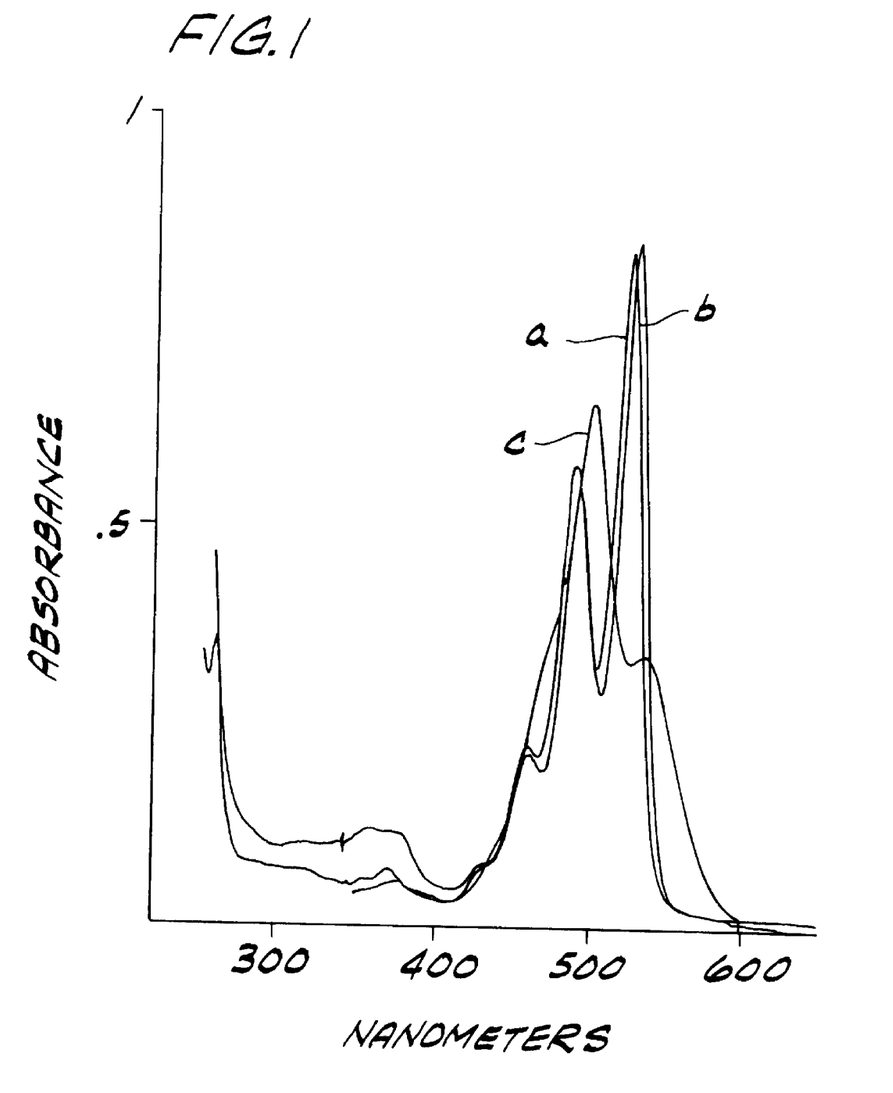
FIG. 1 is a graph showing the absorption spectrum of DAPER in (a) ethanol, (b) dimethyl sulfoxide, and (c) water.
Figure 2:
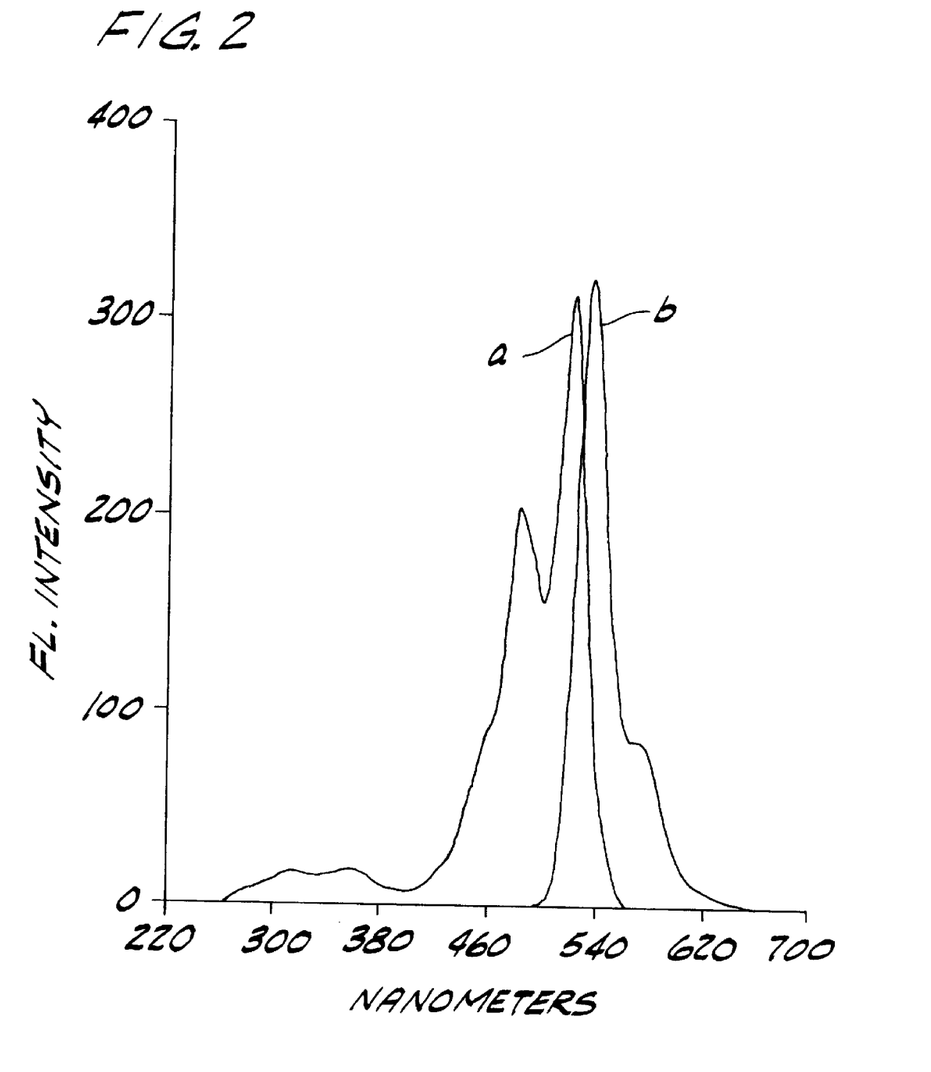
FIG. 2 is a graph showing the fluorescence spectra of DAPER in ethanol; (a) excitation spectrum, emission monitored at 533 nm, (b) emission spectrum, excitation at 523 nm.

The amount of DNA precipitated and recovered from a given sample may be readily determined by measuring either the absorbance or fluorescence of the DAPER dye in the solvent DAPER extract. For example, direct measurement of the absorbance at 525 nm in a 1 ml phenol:chloroform extract was found sufficient for quantitation of ≧2 μg of precipitated DNA. Smaller DNA amounts may be quantitated by measuring the fluorescence of the solvent DAPER extracts. As shown in FIGS. 1 and 2, the absorption and fluorescence properties of DAPER are strongly solvent dependent, and optimal fluorescence has been observed at 532 nm when the solvent DAPER extract was diluted with glycerol:methanol (1:1) with excitation at 523 nm. FIGS. 1 and 2 also show the strong fluorescence and high molar absorbances which were observed for uncharged DAPER in polar organic solvents. Small red shifts of absorbance maxima were observed when the polarity of the solvent was increased. The intensity of fluorescence decreased with solvent in the following order: glycerin>methanol, dimethylformamide, dimethyl sulfoxide>ethanol>>water.

The precipitation, recovery and quantitation of DNA through the practice of the present invention affords several advantages over conventional methodology. The precipitation of DNA with DAPER is rapid, relatively insensitive to DNA length, concentrations or interference by extraneous salt, and requires only standard reagents and micro-scale techniques. Through the practice of the invention, several DNA samples can be precipitated, recovered and quantitated in about one hour. While the mechanism of DNA precipitation by DAPER has not been elucidated, a parallel arrangement of anionic DNA helices and cationic dye stacks is consistent with the apparently strong stacking tendency of the DAPER dye and the observed dye:DNA stoichiometry of the stable complex. Finally, the recovered DNA is highly purified and suitable for direct treatment with restriction endonucleases and other enzymes.

The following examples illustrate the practice of the invention.

Chemicals for syntheses were purchased from Aldrich Chemical Co. and used without further purification. Restriction endonucleases and other enzymes were purchased from Promega or Boehringer Mannheim. Enzyme reactions were carried out under the optimal conditions suggested by the supplier. Calf thymus DNA was prepared from oligonucleosomes isolated from glands as described previously (Strzelecka, T. E. and Rill, R. L., 1987, Journal of the American Chemical Society 109, 4513–4518) and sonicated to an average length of about 300 bp.

DNA restriction endonuclease fragments of the following lengths were prepared from the plasmid pGEM-3Zf(+) (Promega) digested with the indicated enzymes: 3 kbp and 310 bp, EcoR I/Nae I; 100 bp, EcoR I/Hind III; 68 bp, 310 bp, Bsto I. Fragments were separated by chromatography on Bio-Gel A-50 or electrophoresis on 1% agarose and recovered by standard procedures. Radiolabeling on the 3'-end was carried out by reverse transcriptase (AMV) using $\alpha\text{-}^{32}\text{P-}$ATP. Labeled DNA fragments were separated by electrophoresis on an 8% nondenaturing polyacrylamide gel and recovered by soaking (Sambrook, J. et al., 1989, Molecular Cloning, Cold Spring Harbor Laboratory Press).

UV/Visible absorbance spectra were recorded on a Cary 219 spectrophotomer. Fluorescence spectra were recorded on a Perkin-Elmer LS-50 luminescence spectrophotomer. Scintillation counting was carried out on a Beckman-7000 LS counter. Samples were dissolved in 200 $\mu$l of water and 10 ml of Cytoscint (ICN).

EXAMPLE 1
Preparation of N,N'-bis[3,3'-(dimethylamine)propylamine]-3,4,9,10-perylenetetracarboxylic diimide (DAPER)

Three (3) grams of 3,4,9,10-perylenetetracarboxylic dranhydride were mixed with 1.8 ml of N,N-dimethylaminopropylamine in 10 ml of 1,4-dioxane and 10 ml of dimethylformamide (DMF). The mixture was mildly refluxed for 4 hr., then distilled under reduced pressure to remove solvent. The residue was dissolved in about 40 ml water and insoluble compounds were removed by filtration. The pH was adjusted to about 3 with HCl and the solution was allowed to stand for 10 hr. Precipitated byproducts were removed by filtration. The pH of the solution was raised to about 10 with NaOH and the precipitated product was recovered by filtration, washed with water, then vacuum dried overnight. Dark red crystals were obtained in about 75% yield. MS. Calculated for ($C_{34}H_{32}N_4O_4$) 560, found m/z 561 (M+ +1). Proton NMR spectra were not observed in water or methanol, presumably due to aggregation.

EXAMPLE 2
DNA Precipitation, Recovery and Quantitation of DNA

The following procedure was standard for recovery and quantitation of DNA from solutions $\leq$50 $\mu$g DNA/ml in a volume of $\leq$1 ml using a microcentrifuge. Preliminary experiments were performed with slight modifications of this procedure. A stock solution of 1 mM DAPER (0.56 mg/ml) was prepared in 10 mM MES buffer (adjusted to pH 6.5 with NaOH) and stored in the cold protected from light. Precipitation procedures were carried out under normal lighting. One-fifth volume of 1 mM DAPER was added to DNA solutions. After equilibration for 10 min. at room temperature, the precipitates were collected by centrifugation for 5 min. in a microcentrifuge (ca. 11,000 rpm). To remove weakly bound DAPER dye, the pellets were washed twice with 0.5 ml distilled water by vortexing for about 10 sec., then centrifuging for 2 min. Pellets containing as little as 1 $\mu$g DNA were readily observable because of their dark red color. The pellets were resuspended in a desired final volume (typically 20–100 $\mu$l) of 10 mM Tris-HCl buffer, pH=9.40. DAPER dye was extracted from the suspensions by addition of 0.25 ml of phenol(pre-equilibrated with 10 mM Tris-HCl, pH=9.4) plus 0.25 ml chloroform: isoamyl alcohol (24:1). Extraction was repeated once, then the upper aqueous phases containing DNA were carefully removed to fresh tubes using a fine tip pipet. The combined organic phases from the two extractions were used for DNA quantitation. The aqueous DNA solutions were extracted four times with ethyl ether at 0° C. to remove phenol if they were to be used for enzyme reactions. Samples for electrophoresis were applied directly to gels.

The amount of DNA precipitated from a given sample was determined by measuring either the absorbance or fluorescence of the DAPER dye in the phenol: chloroform extract. Direct measurement of the absorbance at 525 nm in the 1 ml phenol: chloroform extract was sufficient for quantitation of $\geq$2 $\mu$g of precipitated DNA (see Example 3). Smaller DNA amounts were quantitated by measuring the fluorescence of extracts. The absorption and fluorescence properties of DAPER are highly solvent dependent. Optimal fluorescence was observed at 532 nm if the extracts were diluted with an equal volume of glycerol: methanol (1:1) with excitation at 523 nm.

EXAMPLE 3
Absorption and Fluorescence Spectra of DAPER

The visible absorption and fluorescence spectra of DAPER were found to be strongly dependent on solvent. FIG. 1 shows the absorption spectrum of DAPER in (a) ethanol ($2\cdot10^{-5}$M), (b) dimethyl sulfoxide ($1.5\cdot10$–5M ), and (c) water ($3.7\cdot10^{-5}$M), and (c) water ($3.7\cdot10^{-5}$M). Concentrations of DAPER are given in parentheses. FIG. 2 shows the fluorescence spectra in ethanol with the DAPER concentration being approximately $1\times10^{-6}$M and (a) excitation spectrum, emission monitored at 533 nm and (b) emission spectrum, excitation at 523 nm. As shown, strong fluorescence and high molar absorbencies were observed for uncharged DAPER in polar organic solvents. Small red shifts of absorbance maxima were observed when the polarity of the solvent was increased. The intensity of fluorescence decreased with solvent in the following order: glycerin$\geq$methanol, dimethylformamide, dimethyl sulfoxide$\geq$ethanol>>water. Fluorescence was not observed in aqueous solutions near neutral pH, either in the presence or absence of DNA. Visible absorption spectra of the dication obtained in water were markedly distorted and hypochromic relative to spectra recorded for the neutral species in organic solvents. In aqueous solution, there was a broad band centered at about 497 nm, with a weak shoulder at 530 nm. Greater spectral resolution was observed in organic solvents, with the maximal absorbance at about 525 nm, a slightly weaker band at about 486 nm, and yet a weaker band at about 445 nm (see FIG. 1). Increasing the ionic strength of aqueous solutions from 10 mM to 500 mM by adding NaCl caused additional spectral shifts and reduced the absorbance at 497 nm by about 40%. A linear decrease in absorbance was observed with log (ionic strength). It is believed in explanation of these phenomena that the salt suppresses electrostatic self-repulsions and favors stacking interactions which cause the observed hypochromism and bathochromism.

Despite this evidence for stacking in water, Beer's law was obeyed over the entire absorbance range spectrally accessible down to about 0.3 $\mu$M DAPER (observed in a 10 cm path length cell), suggesting that extensive stacking occurs below this limit. Obvious deviations from Beer's law were observed for micromolar concentrations of uncharged DAPER in methanol and ethanol, suggesting that stacking also occurs in these solvents.

EXAMPLE 4
DNA Precipitation by DAPER

Precipitation of DNA by DAPER was observed while attempting to measure its DNA binding affinity by spectroscopic titration. In order to develop a DNA isolation and analysis method based on this phenomenon, it was necessary to characterize the DAPER:DNA precipitates and possible influences on the precipitation. The concentration of DAPER required for complete DNA precipitation was investigated using a $^{32}$P-end-labeled EcoR I/Nae I fragment of pGEM-Zf(+)(310 bp) mixed with a 10-fold excess of sonicated calf thymus DNA in MES buffer containing 100 mM NaCl. Samples were treated with various DAPER concentrations, then recoveries of DNA in the supernatants and pellets were measured by scintillation counting and by autoradiography of electropherograms. Precipitation was first noted at a DAPER:DNA ratio of 1:3 moles DAPER per mole DNA base) and was complete at a ratio of 3:2. Precipitation was complete at this DAPER: DNA ratio, even when the DNA concentration was only 50 ng/ml.

Figure 3:
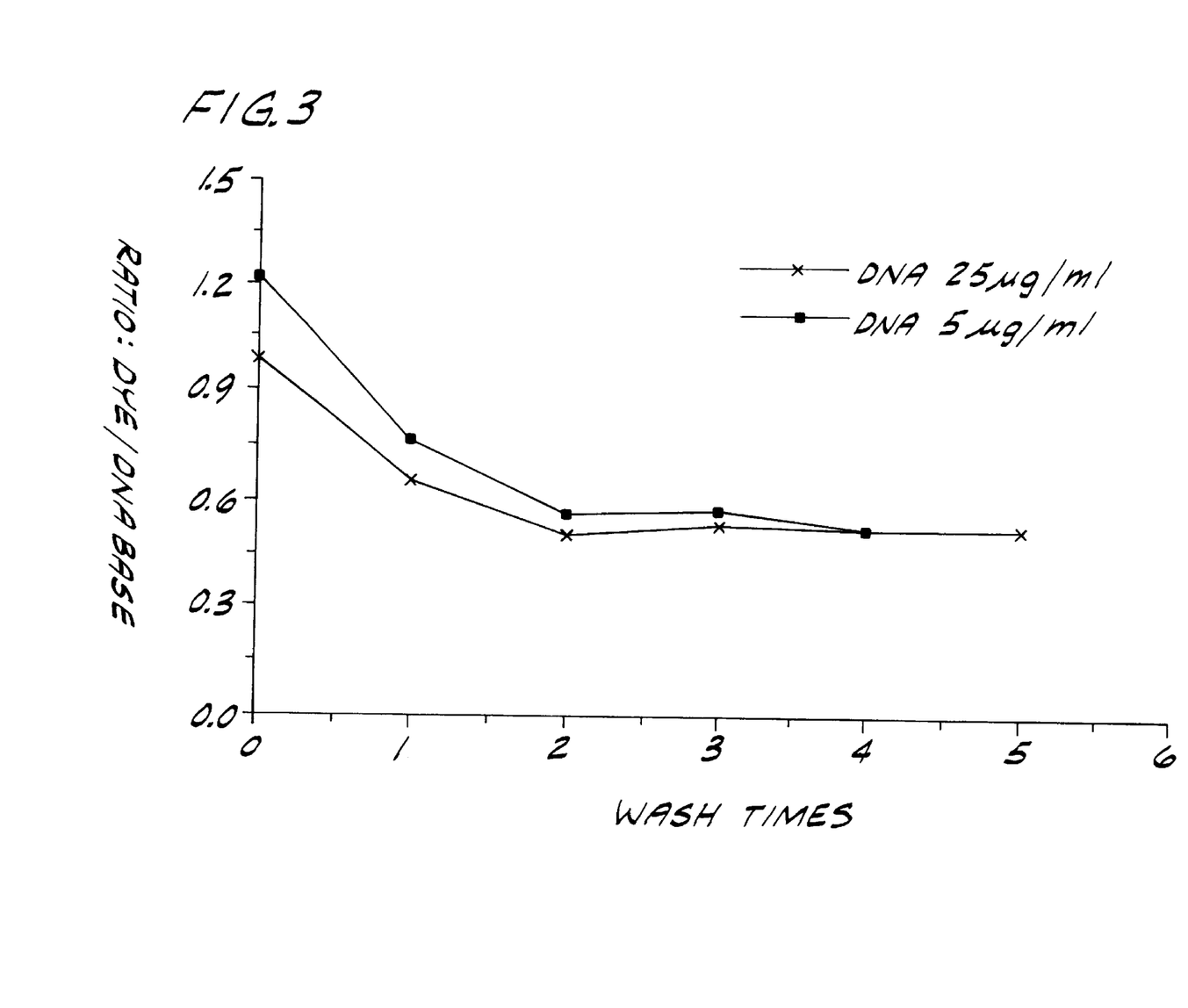
FIG. 3 is a graph showing the dependence of DAPER to DNA base molar ratio in the precipitates on the extent of washing of precipitates of DNA/DAPER complex with water.

Sodium chloride concentrations up to 0.5M had no influence on precipitation efficiency, but reduced yields were noted in 1M NaCl. The amount of DAPER precipitated with DNA increased with increasing salt concentration from one dye per base pair in very low ionic strength buffer, to three dyes per base pair in $\geq$0.2M NaCl. The DAPER dye recovered in excess of charge equivalency was very weakly bound, however, and was readily removed by washing the pellets with distilled water. By contrast, the neutral, single dye/base pair complex was stable to repeated washes. FIG. 3 shows the dependence of DAPER to DNA base molar ratio on the extent of washing of precipitates of DNA/DAPER complex, with 200 μl water being used for each wash. The final DAPER:DNA ratio was not significantly affected by the initial DNA concentration.

Figure 4:
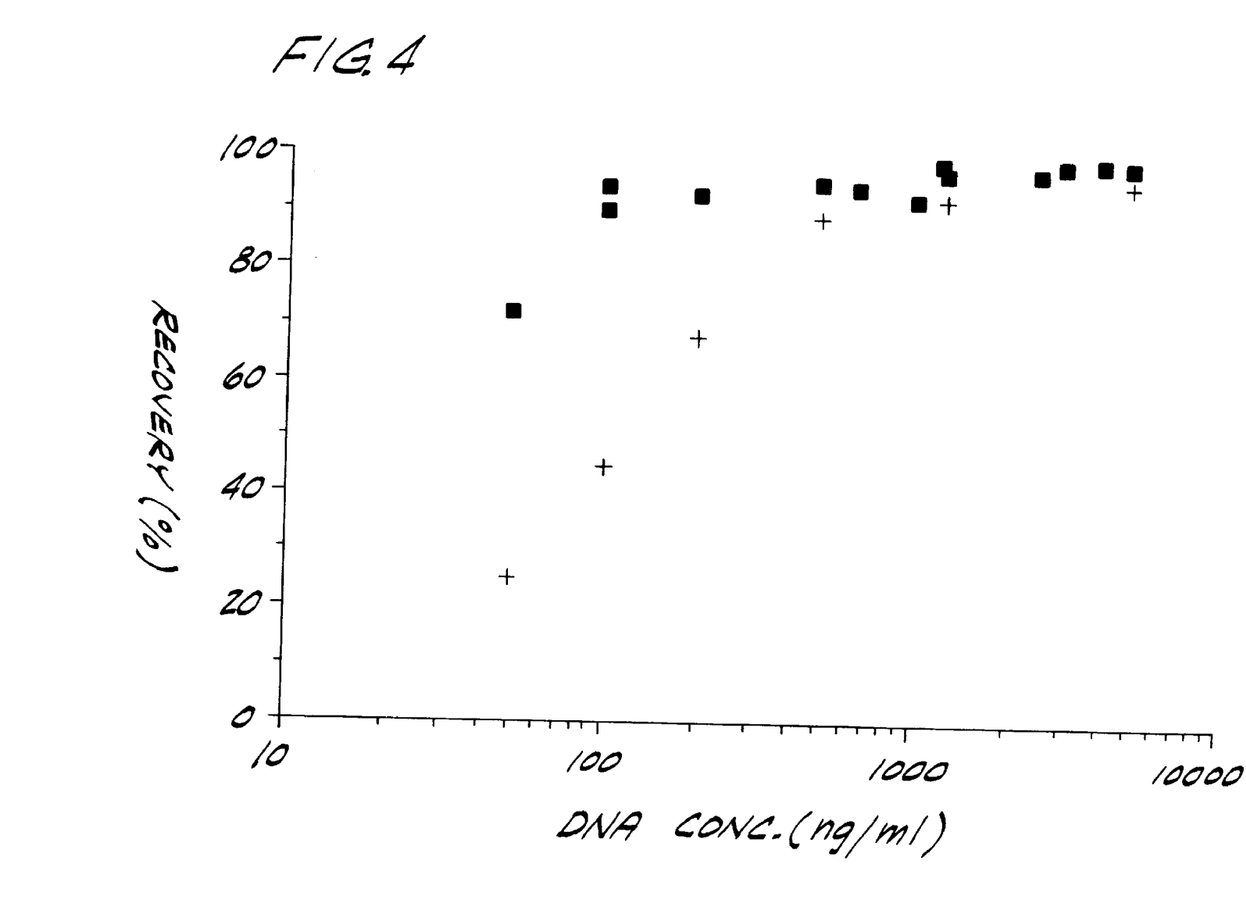
FIG. 4 is a graph showing a comparison of the recovery of DNA by DAPER precipitation ( ■) or isopropanol precipitation (+)

EXAMPLE 5
Comparative Efficiency of DNA Recovery With DAPER and Isopropanol DNA recovery was further tested and compared to traditional isopropanol precipitation (Sambrook, J. et al., 1989, supra). Samples of $^{32}$P-labeled DNA fragment (EcoR I/Nae I fragment of pGEM-Zf(+) plasmid, 310 bp) plus a 20-fold excess of calf thymus DNA were precipitated by DAPER at room temperature in 10 min. as previously described, or by adding 0.5 volumes of isopropanol with overnight storage at –20° C. Recoveries were calculated based on either the DNA absorbance at 260 nm or, in the case of trace amounts of DNA, by scintillation counting. The results are shown in FIG. 4. At relatively high DNA concentrations (>500 ng/ml), both methods gave satisfactory recoveries>90%. The recovery by isopropanol precipitation decreased dramatically below 500 ng DNA/ml. By contrast, DNA recovery by DAPER precipitation was >90% complete down to a concentration of 100 ng/ml, and even with 50 ng/ml DNA, the recovery was 73%.

The efficiency of DNA recovery by ethanol or isopropanol precipitation is largely affected by the length of DNA, decreasing significantly as the DNA length decreases below 300 base pairs. The length dependence of the efficiency of DNA recovery by DAPER precipitation was investigated using different $^{32}$P-labeled restriction endonuclease fragments of pGEM-Zf(+) plasmid. No length dependence of recovery was observed for DAPER precipitation of fragments as small as 68 bp, while large effects were observed for isopropanol precipitation of the smaller fragments as shown by the results set forth in the following Table 1:

TABLE 1

| DNA Length | % Recovery DAPER Precipitation | | % Recovery Isopropanol Precipitation | |
|---|---|---|---|---|
| (bp) | 200 ng/ml | 1 μg/ml | 200 ng/ml | 1 μg/ml |
| 68 | 94 | 96 | 21 | 50 |
| 110 | 95 | 98 | 47 | 66 |
| 310 | 94 | 94 | 68 | 91 |
| 3000 | 96 | 97 | 81 | 95 |

EXAMPLE 6
Suitability of DAPER-Precipitated and Recovered DNA for Enzymatic Reactions Alkaline pH promotes extraction of DAPER from recovered DNA into organic solvents, but could cause DNA strand separation. A weak, moderately alkaline Tris buffer (10 mM, pH 9.4) was found sufficient for extraction of DAPER into a standard phenol:chloroform mixture without adverse effects. Chloroform or phenol alone were less efficient. Four extractions of the aqueous phase containing DNA with diethyl ether appeared sufficient to remove phenol that could interfere with subsequent spectral analyses or enzymatic reactions. The UV/V is absorbance spectrum of DNA ($\geq$25μg/ml) after precipitation and extraction of DAPER showed no traces of absorption by the DAPER in the visible region, indicating that extraction was>99.5% complete and that the residual dye concentration was<5 ng/ml.

Figure 5:
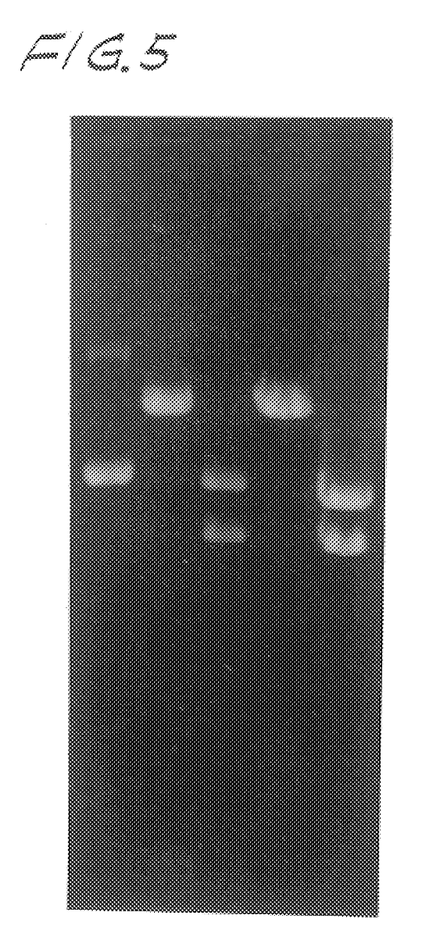
FIG. 5 shows the results of restriction endonuclease digestion of DNA precipitated with DAPER. Lane 1, Plasmid pGEM-Zf(+) recovered by DAPER precipitation; Lane 2, plasmid digested with EcoR I, precipitated with DAPER and recovered for electrophoresis. Lane 3, sample as applied to lane 2 after digestion with Sca I and recovery by DAPER precipitation. Samples for lanes 4 and 5 were analogous to those of lanes 2 and 3 but DNA was recovered by ethanol precipitation. Electrophoresis was preformed on mini-gels of 1% agarose. Band intensities reflect gel loading and not relative recoveries.

In order to determine whether normal enzymatic reactions can be performed on recovered DNA, DNA digestions with restriction endonucleases EcoR I and Sca I were examined using plasmid samples isolated in parallel by either DAPER precipitation or ethanol precipitation. Recovered plasmid was subjected to EcoR I digestion. The DNA fragments were recovered again by both methods, then digested with Sca I. The DNA fragments from all steps were analyzed by gel electrophoresis on 1% agarose. As shown in FIG. 5, almost identical restriction endonuclease patterns were obtained from the DNA isolated by two methods. In a separate experiment, approximately 4 μg each of two DNA restriction fragments 262 and 267 bp long were recovered from about 3 ml of buffer obtained after crushing and soaking of polyacrylamide gel slices. The recovered fragments were 3'-end labeled to high specific activity with AMV reverse transcriptase and α-$^{32}$P-dATP. Thus, the DAPER precipitation and extraction procedures described above appear highly suitable for recovery of functional DNA.

EXAMPLE 7
Measurement of DNA Concentration

Figure 6:
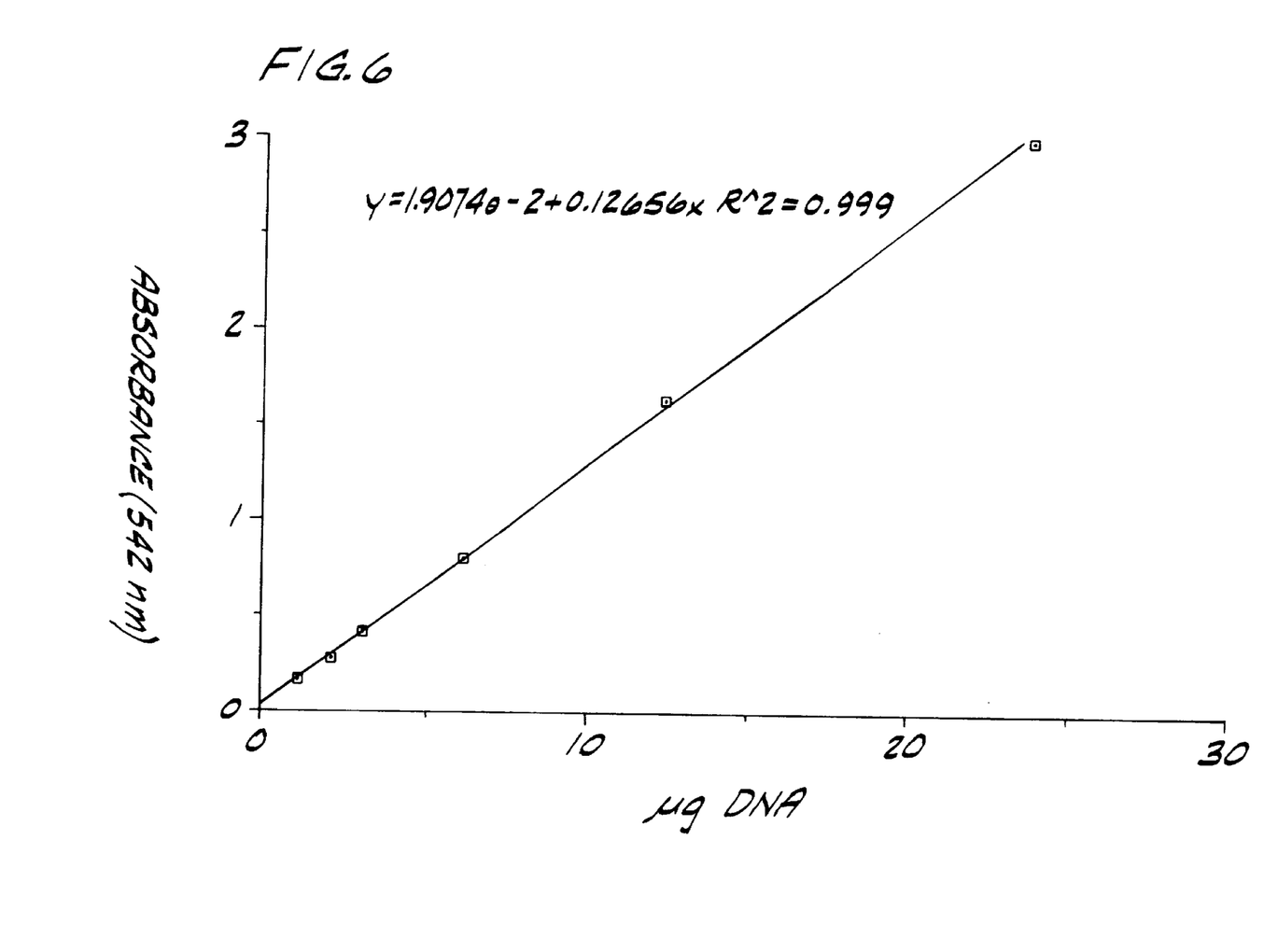
FIG. 6 is a graph showing DNA quantitation based on the absorbance of DAPER in phenol: chloroform extracts.
Figure 7:
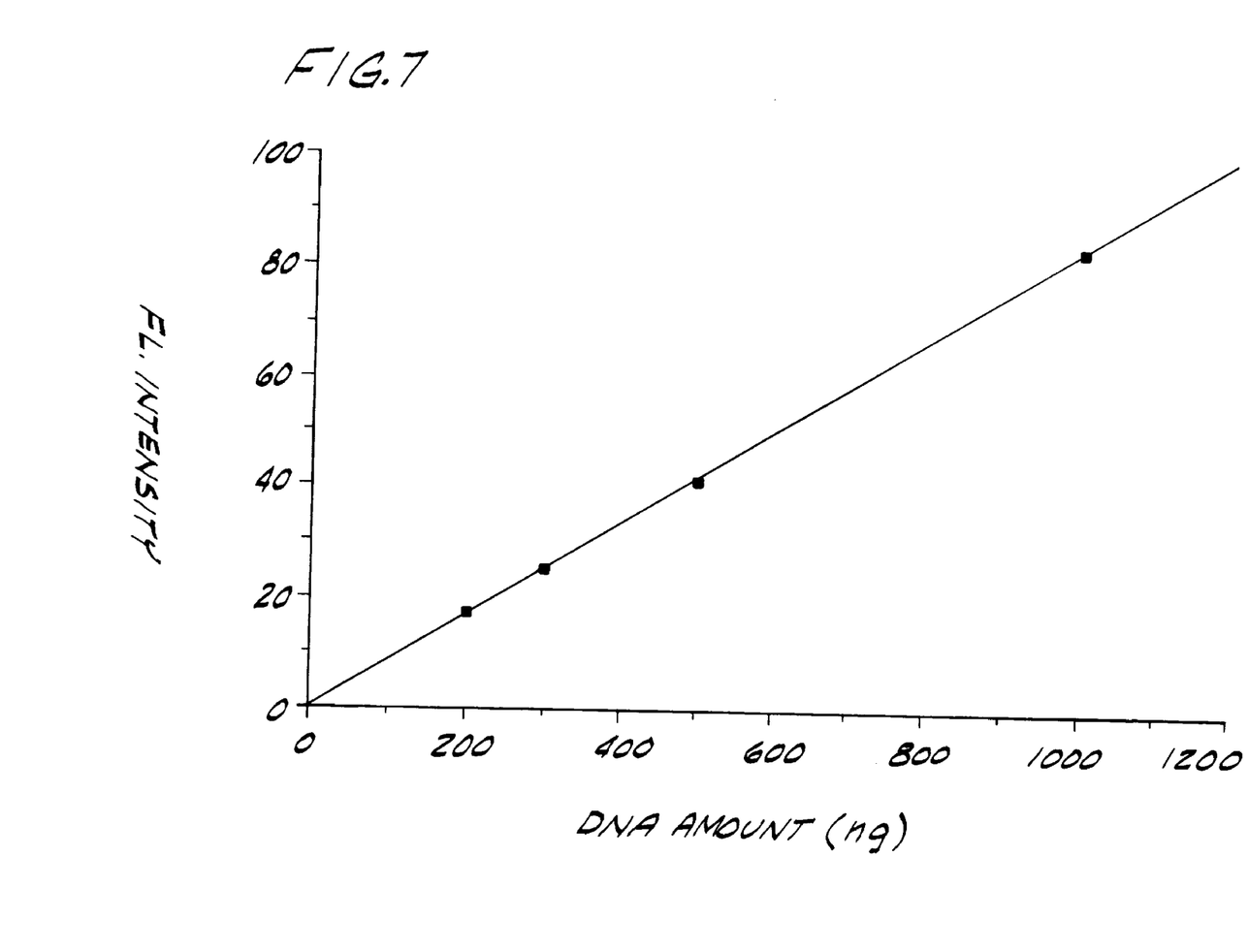
FIG. 7 is a graph showing DNA quantitation based on the fluorescence of DAPER in phenol: chloroform extracts.

In accordance with the present invention, DAPER precipitates DNA quantitatively and stoichiometrically, and the precipitated DAPER can be extracted completely. Since DAPER possesses strong fluorescence emission and light absorption, measurement of either of these quantities can be used to calculate the amount of DNA precipitated. The absorbance and fluorescence intensities of the DAPER extracts were measured in different solvents to determine the ranges of linear response. Below a DAPER concentration of $2 \times 10^{-5}$M Beer's law was well obeyed for absorbance measurements in chloroform, phenol: chloroform or dimethylformamide. A simple measurement of the absorbance of 1 ml of the two combined phenol: chloroform extracts (0.5 ml each) in a small volume, 1 cm pathlength cell provided excellent precision in measuring DNA amounts down to about 2 μg as shown in FIG. 6. Measurement of fluorescence extends the sensitivity at least by a factor of ten if a conventional 3 ml, 1 cm pathlength cell is used and the extract is diluted with a glycerin-methanol mixture (1:1) as shown in FIG. 7. Addition of glycerin to solvents provided significant fluorescence enhancement. Below $2\times10^{-5}$M, the fluorescence intensity was in linear relation with the DAPER concentration in 50% glycerin-50% methanol or 50% glycerin-50% dimethylformamide.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A process for the precipitation, recovery and quantitation of DNA from solutions containing DNA which comprises the steps of:

a. adding N,N'-bis- 3,4,9,10-perylenetetracarboxylic diimide to a solution containing DNA and allowing the resulting mixture to equilibrate;

b. collecting the resulting precipitate;

c. removing weakly bound excess N,N'-bis-3,4,9,10-perylenetetracarboxylic diimide from said precipitate;

d. extracting N,N'-bis-3,4,9,10-perylenetetracarboxylic diimide from said precipitate by the addition of a solvent for N,N'-bis-3,4,9,10-perylenetetracarboxylic diimide; and e. determining the amount of DNA precipitated by measuring either the absorbance or fluorescence of N,N'-bis-3,4,9,10-perylenetetracarboxylic diimide in the solvent extract from step d.

2. A process as set forth in claim 1 wherein said solvent is selected from the group consisting of chloroform, phenol:chloroform and dimethylformamide.

3. A process as set forth in claim 1 wherein N,N'-bis-3,4,9,10-perylenetetracarboxylic diimide is removed from said precipitate in step c by washing the precipitate with water.

* * * * *

UNITED STATES PATENT AND TRADEMARK OFFICE
CERTIFICATE OF CORRECTION

PATENT NO. : 5,811,307
DATED : September 22, 1998
INVENTOR(S) : Randolph L. Rill and Zhi-Ren Liu

It is certified that error appears in the above-identified patent and that said Letters Patent is hereby corrected as shown below:

Column 9,
Line 22, "N,N'-bis-3,4,9,10-" should read
-- N,N'-bis[3,3'-(dimethylamino)propylamine]-3,4,9,10- --.

Column 10,
Lines 2, 5, 7, 11-12 and 17-18 "N,N'-bis-3,4,9,10-" should read
-- N,N'-bis[3,3'-(dimethylamino)propylamine]-3,4,9,10- --.

Signed and Sealed this

Ninth Day of March, 2004

JON W. DUDAS
*Acting Director of the United States Patent and Trademark Office*